United States Patent
Knorr et al.

(10) Patent No.: US 6,970,571 B2
(45) Date of Patent: Nov. 29, 2005

(54) LOW COST HEARING PROTECTION DEVICE

(75) Inventors: Jon P. Knorr, Grand Rapids, MI (US); Benjamin P. Knapp, Byron Center, MI (US)

(73) Assignee: Jackson Products, Inc., St. Charles, MO (US)

( * ) Notice: Subject to any disclaimer, the term of this patent is extended or adjusted under 35 U.S.C. 154(b) by 46 days.

(21) Appl. No.: 10/356,914

(22) Filed: Feb. 3, 2003

(65) Prior Publication Data

US 2003/0223612 A1 Dec. 4, 2003

Related U.S. Application Data

(60) Provisional application No. 60/353,760, filed on Feb. 2, 2002.

(51) Int. Cl.[7] ............................................... H04R 25/00
(52) U.S. Cl. ........................ 381/370; 381/102; 381/106; 381/107
(58) Field of Search ............................ 381/57, 74, 72, 381/73.1, 71.6, 370, 371, 120, 56, 102, 106, 107, 312, 320, 321

(56) References Cited

U.S. PATENT DOCUMENTS

| | | | |
|---|---|---|---|
| 3,920,931 A | | 11/1975 | Vanick, Jr. |
| 4,052,571 A | | 10/1977 | Gregory et al. |
| 4,099,035 A | | 7/1978 | Yanick |
| 4,118,604 A | | 10/1978 | Yanick |
| 5,278,912 A | | 1/1994 | Waldhauer |
| 5,355,418 A | | 10/1994 | Kelsey et al. |
| 5,706,357 A | * | 1/1998 | Yang .......................... 381/107 |
| 5,815,582 A | | 9/1998 | Claybaugh et al. |
| 6,072,885 A | | 6/2000 | Stockham, Jr. et al. |
| 6,330,339 B1 | * | 12/2001 | Ishige et al. ................ 381/312 |
| 2001/0046304 A1 | | 11/2001 | Rast |

* cited by examiner

*Primary Examiner*—Huyen Le
(74) *Attorney, Agent, or Firm*—Dunlap, Codding & Rogers, P.C.

(57) ABSTRACT

An earmuff comprising a headpiece and a circuit. The headpiece supports the earmuff on the head of an individual. The circuit has an input device for receiving external sound energy and converting the external sound energy to electrical sound signals.

1 Claim, 12 Drawing Sheets

LOW COST HEARING PROTECTION DEVICE

CROSS-REFERENCE TO RELATED APPLICATIONS

This application claims priority to the provisional application identified by U.S. Ser. No. 60/353,760, filed on Feb. 2, 2002, the entire content of which is hereby incorporated herein by reference.

STATEMENT REGARDING FEDERALLY SPONSORED RESEARCH AND DEVELOPMENT

Not Applicable.

BRIEF DESCRIPTION OF THE SEVERAL VIEWS OF THE DRAWING

FIG. 1b is a side view of the apparatus depicted in FIG. 1a.

DETAILED DESCRIPTION OF THE INVENTION

Referring now to the drawings and in particular to FIGS. 1a–1e, shown therein and designated by a reference numeral 10 is an apparatus constructed in accordance with the present invention for attenuating or enhancing sounds exceeding a predetermined level thereby protecting an individual's hearing. In one preferred embodiment, the apparatus 10 permits the individual to set the volume of sounds passed through the apparatus 10 to the individual's ears and selectively attenuates the magnitude of the sounds, in real-time, based on the volume setting and a predetermined sound profile programmed into the apparatus 10. The pre-determined sound profile can be modified or tailored to certain environments so that the acoustical characteristics of the apparatus 10 can be customized without modifying the hardware of the apparatus 10 thereby reducing the manufacturing costs of apparatus 10. The apparatus 10 shown in FIG. 1 is exemplified as a headset for use as a noise abatement headset, but could be exemplified as a single ear headset, an ear bud style device, or a hearing aid.

The apparatus 10 is provided with a head piece 12 supporting two earpieces 14a and 14b. Each of the earpieces 14a and 14b have a cushioned inner face 16a and 16b, and an inner cup portion 18a and 18b retaining a speaker 20a and 20b. The speakers 20a and 20b are each acoustically coupled to the ear canal when the apparatus 10 is being worn by an individual. Each of the ear pieces 14a and 14b also supports a microphone 22a and 22b configured to receive sound energy which occurs external to the earpieces 14a and 14b (hereinafter referred to as "external sound energy") and to convert the external sound energy to electrical sound signals. The electrical sound signals are indicative of the sound energy received by the microphones 22a and 22b. The microphones 22a and 22b can be any type of suitable microphones, such as condenser microphones.

The apparatus 10 is also provided with a circuit 24, and a sound control device 26. The circuit 24 receives the electrical sound signals produced by the microphones 22a and 22b and drives the speakers 20a and 20b for selectively coupling the external sound energy to at least one of the individual's ear canals when the apparatus 10 is worn by the individual. The sound control device 26 has buttons or knobs which can be manipulated by the individual to control certain operations of the apparatus 10. The control device 26 is implemented by way of example as a keypad. The control device 26 can be provided as a separate unit, attached to the head piece 12, or attached to and supported by one of the earpieces 14a and 14b. As will be discussed below, the control device 26 is preferably provided with an on/off button 30, an up-volume button 32, a down-volume button 34, a left balance button 36, and a right balance button 38.

Figure 1A:
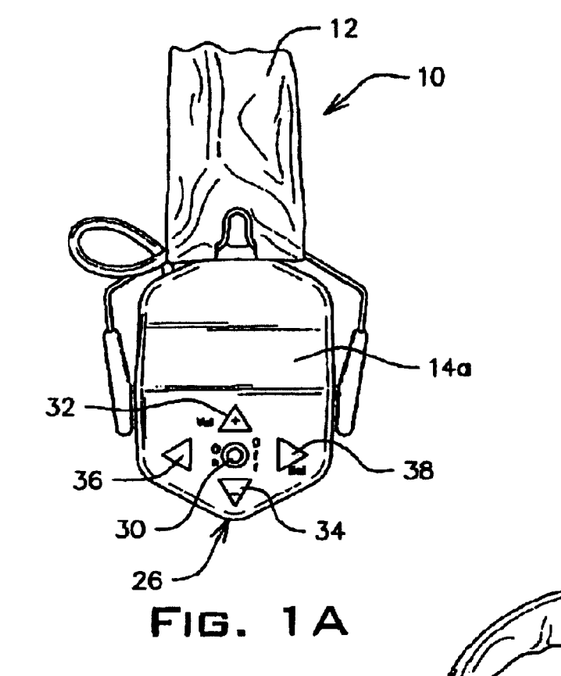
FIG. 1a is a perspective view of an apparatus constructed in accordance with the present invention for attenuating sounds exceeding a predetermined level thereby protecting an individual's hearing.
Figure 1B:
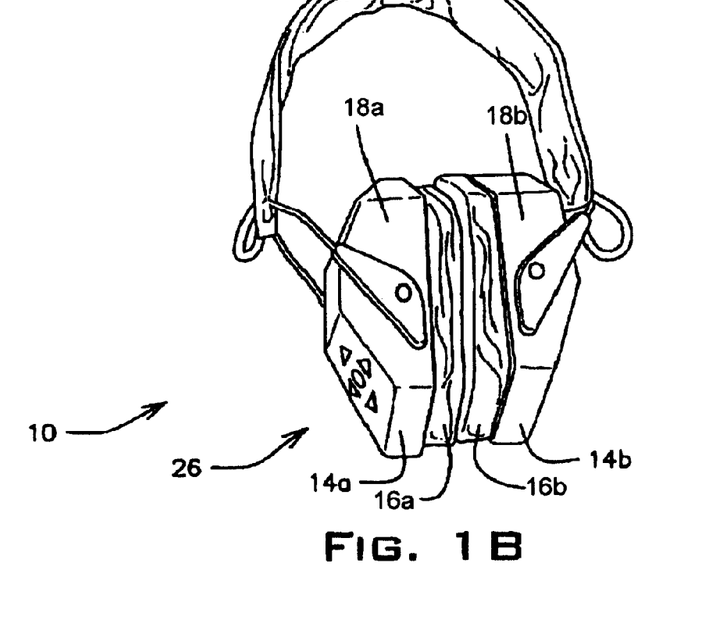
Figure 1C:
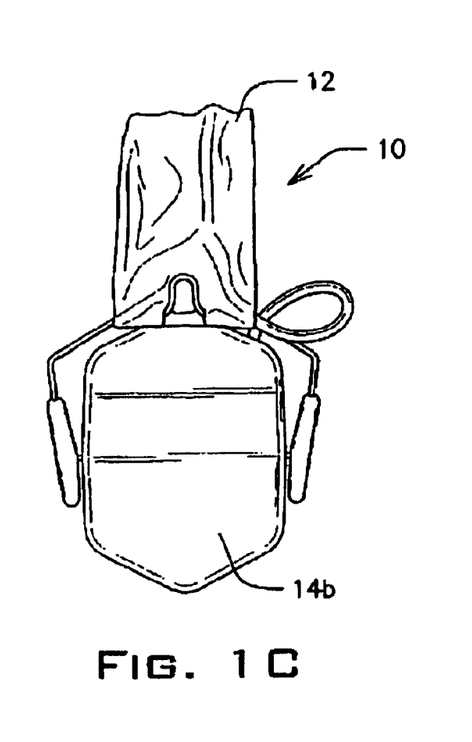
FIG. 1c is a perspective view of the apparatus depicted in FIG. 1a, wherein an opposite side of the apparatus is shown
Figure 1D:
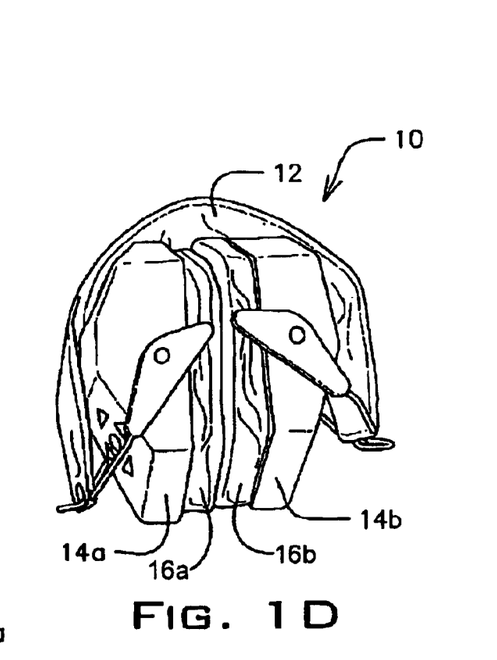
FIG. 1d is a side view of the apparatus in a folded condition.
Figure 1E:
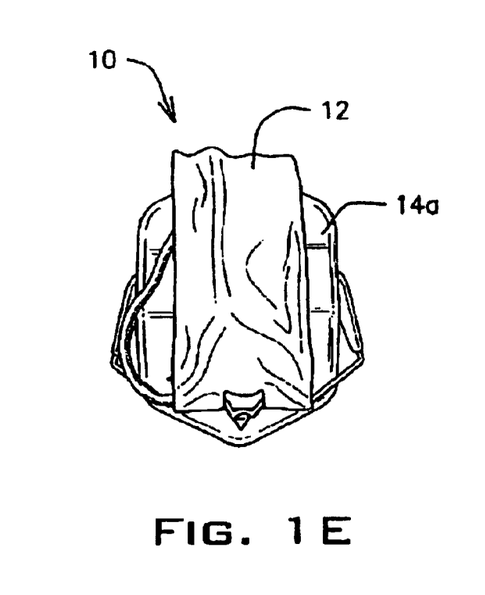
FIG. 1e is a top plan view of the apparatus shown in FIG. 1d.
Figure 2:
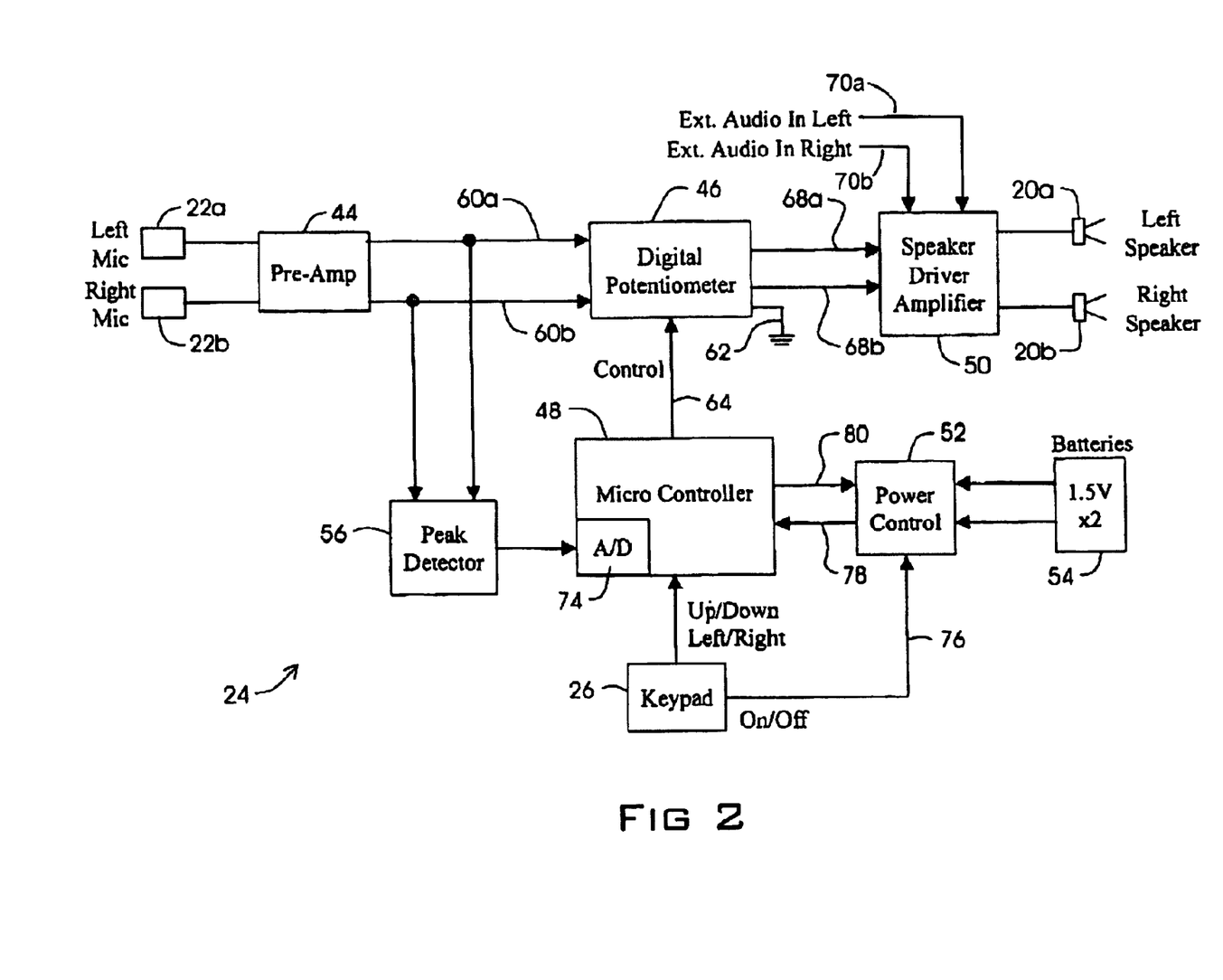
FIG. 2 is a block diagram of a circuit constructed in accordance with the present invention.
Figure 3:
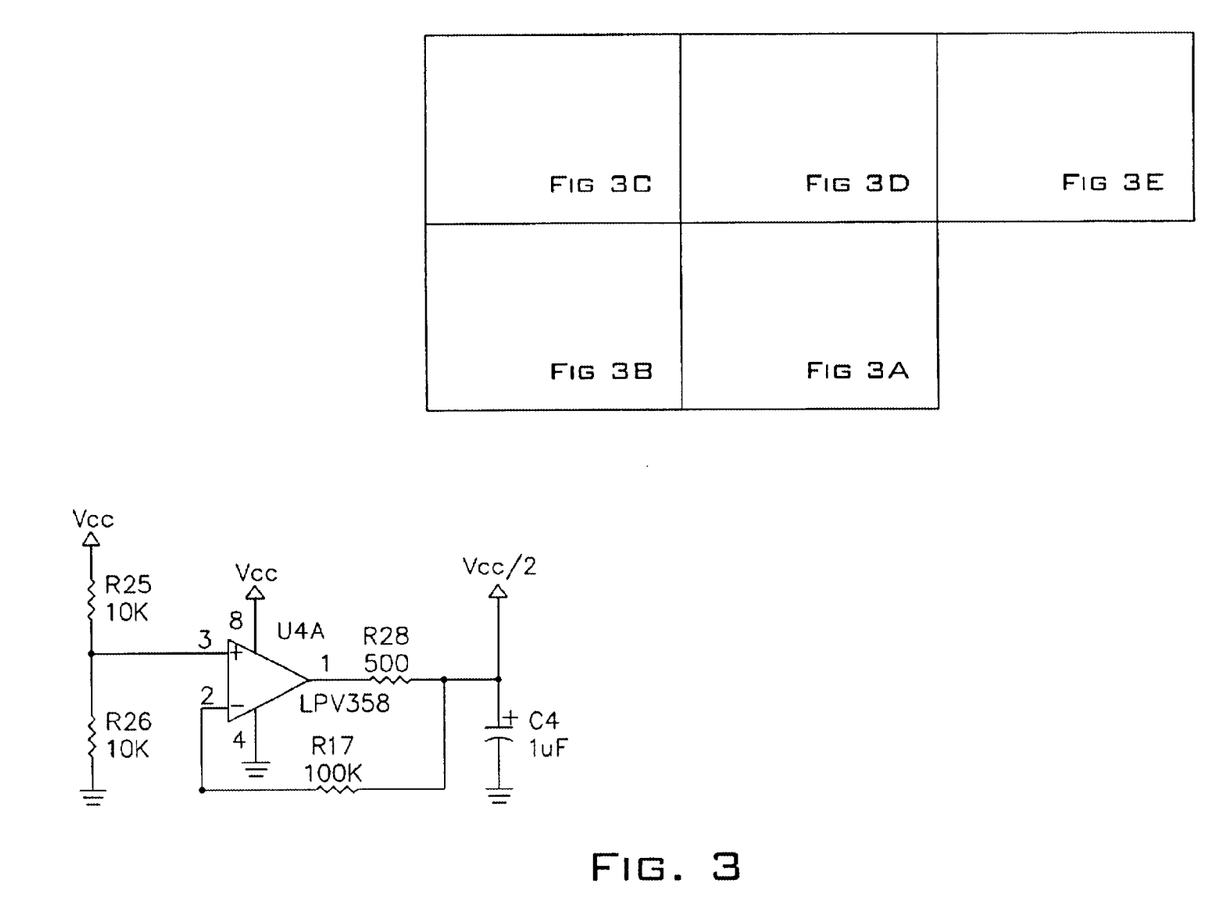
FIG. 3 is a schematic diagram of the hearing protection circuit depicted in FIG. 2.
Figure 3A:
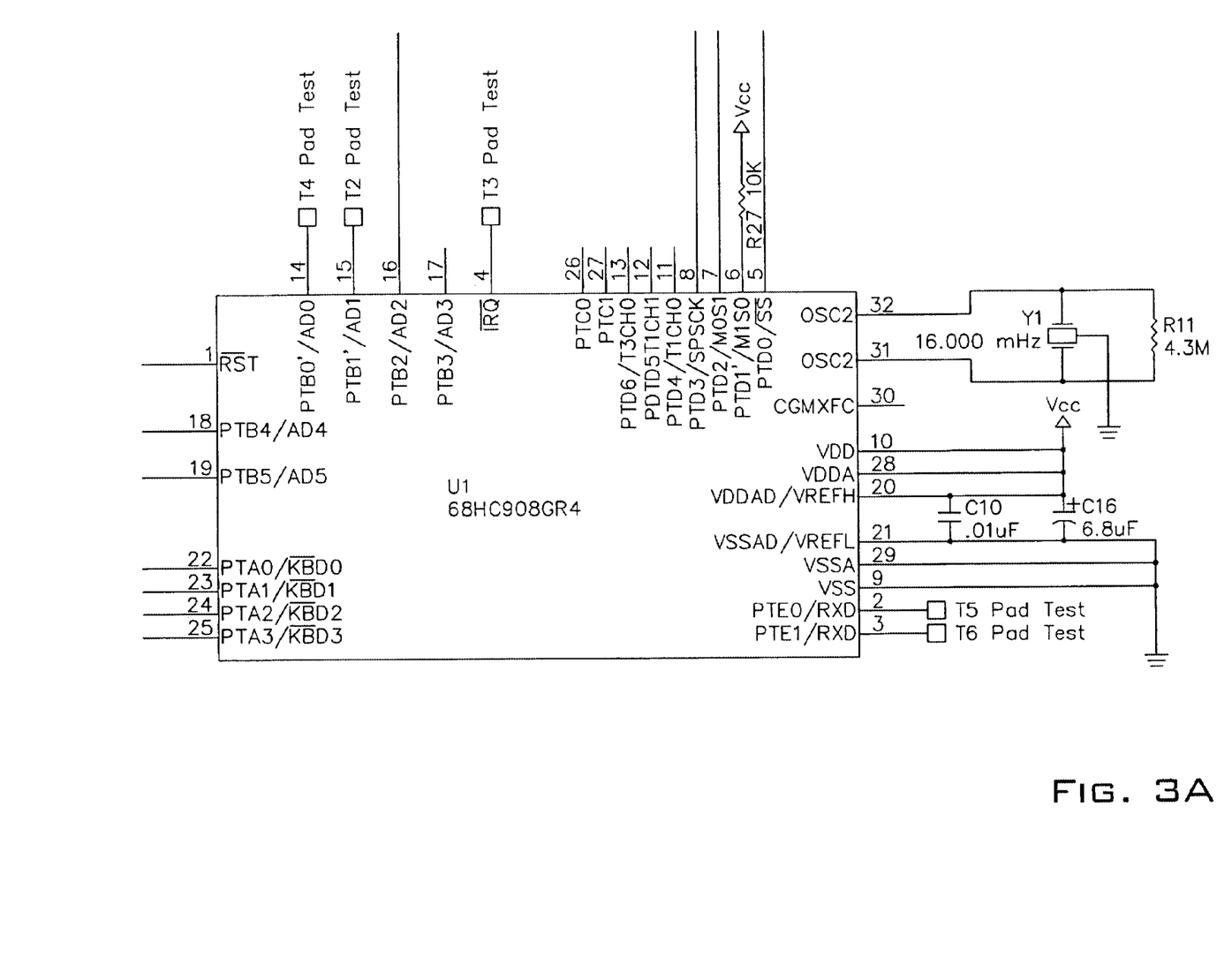
Figure 3B:
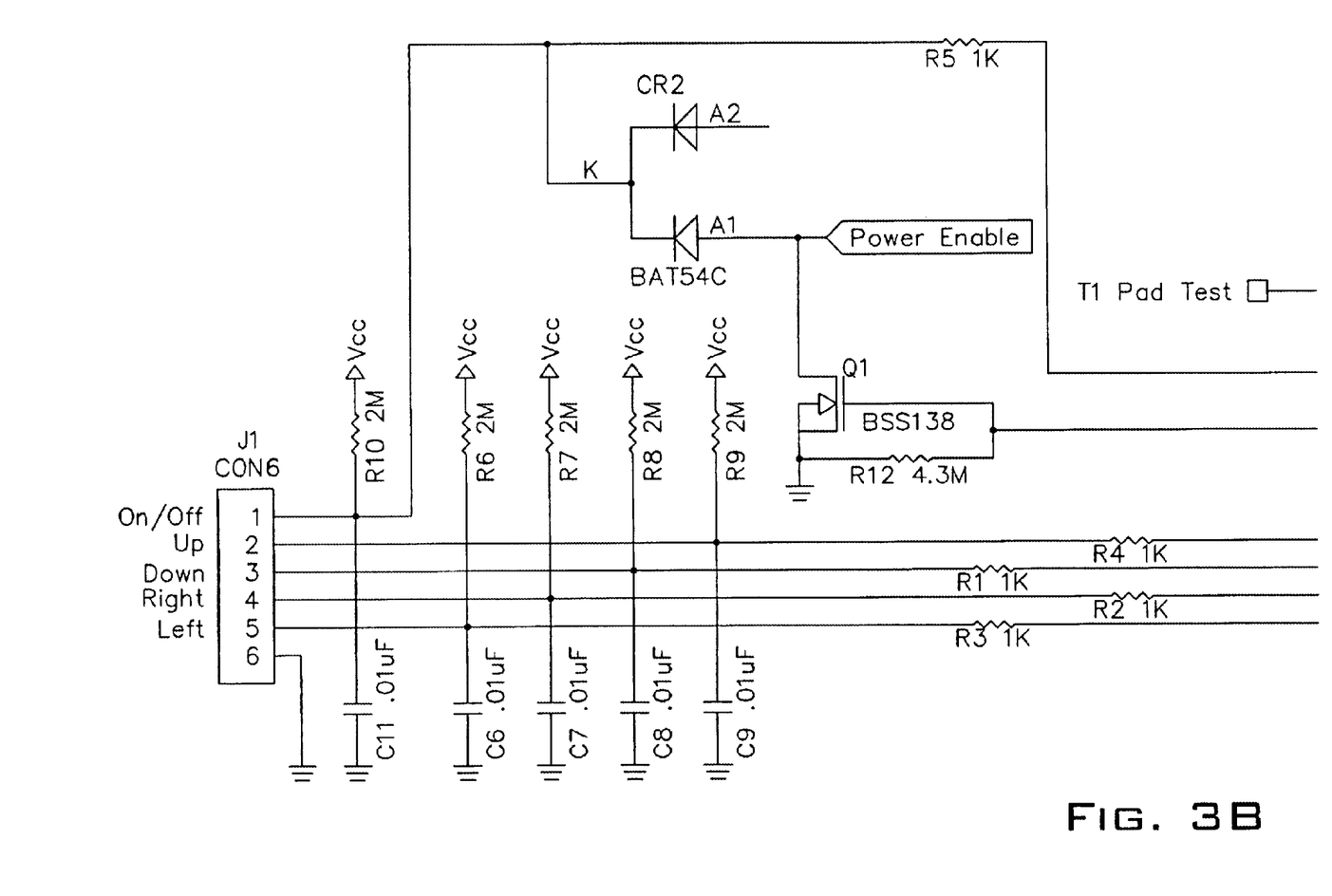
Figure 3C:
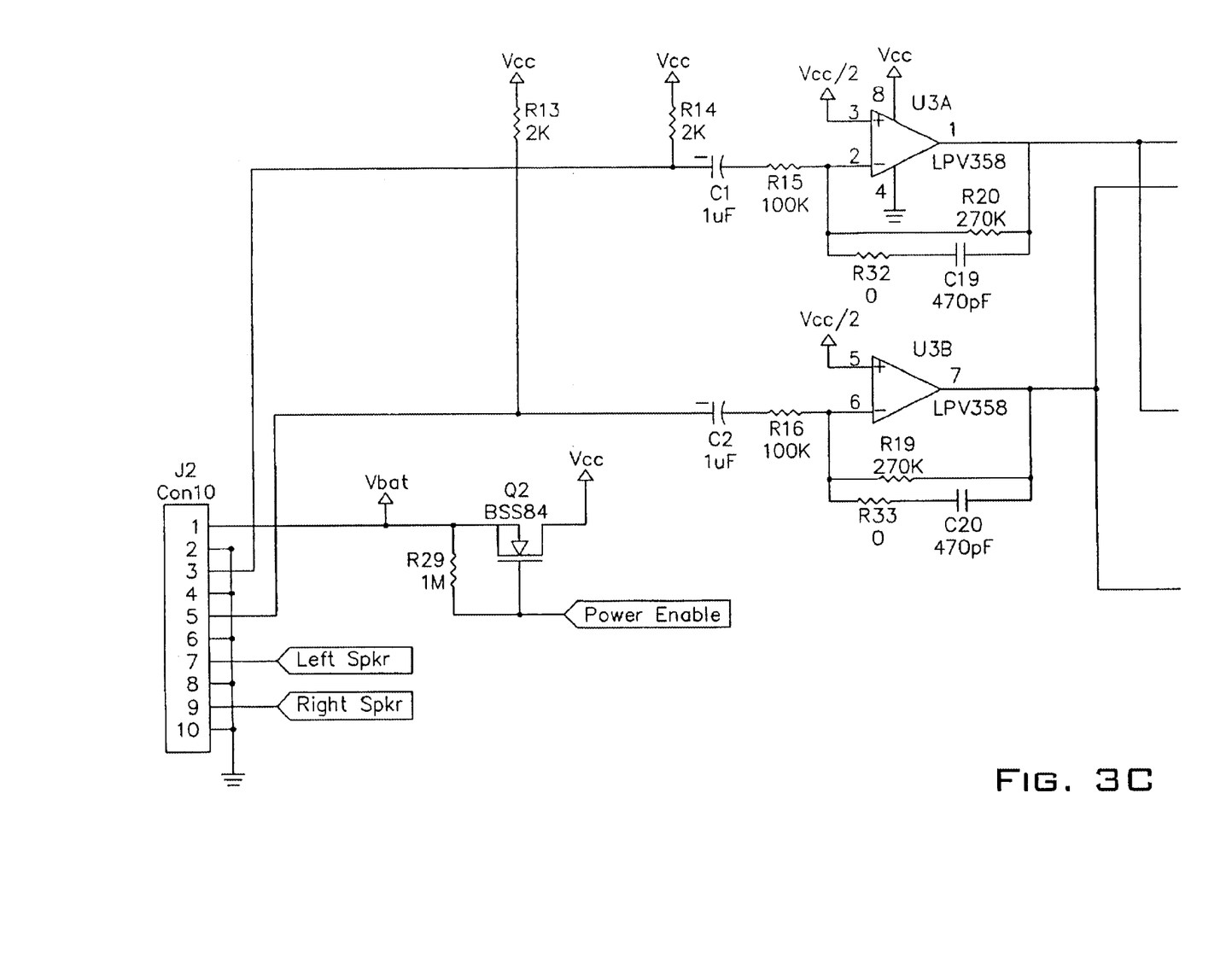
Figure 3D:
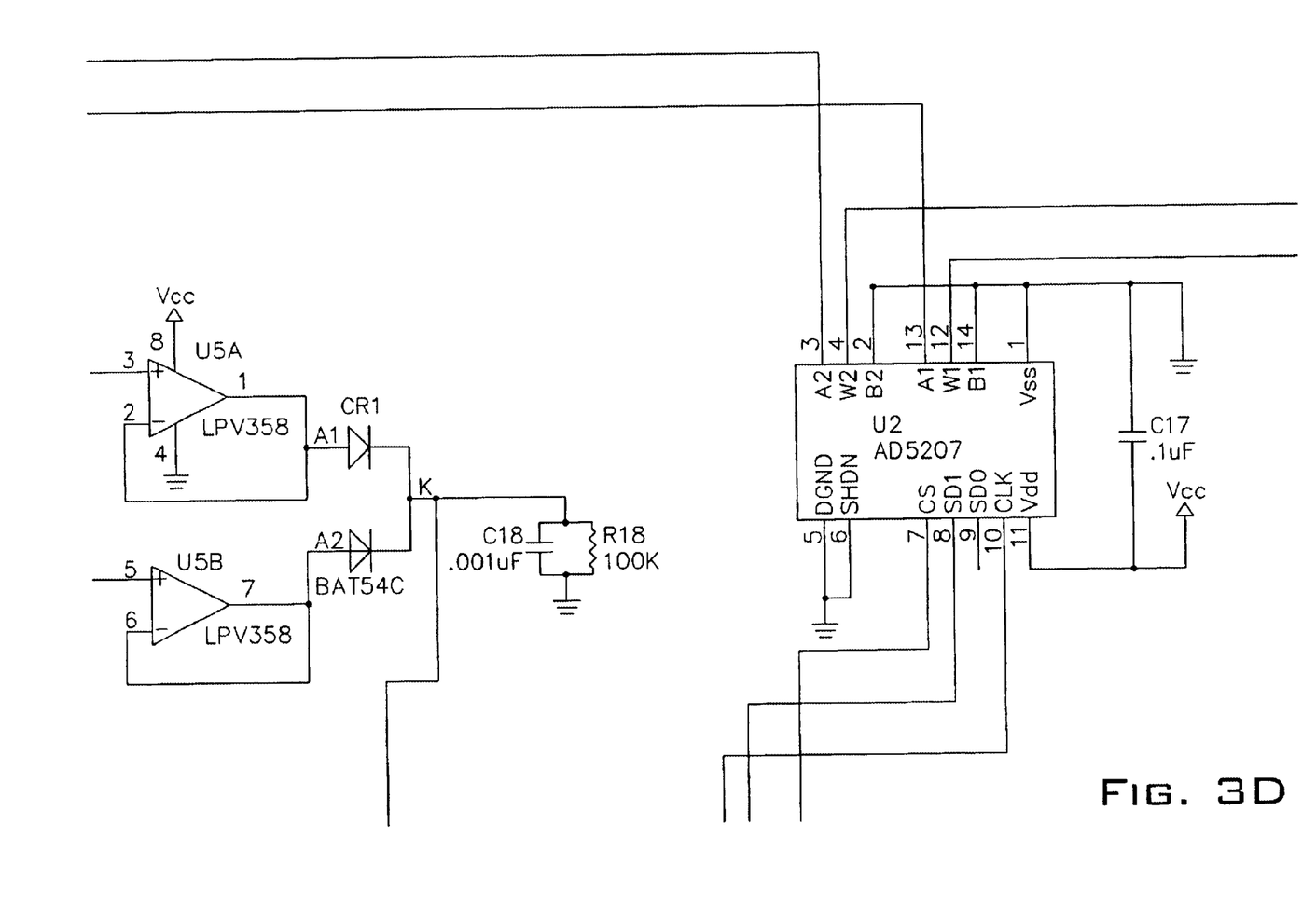
Figure 3E:
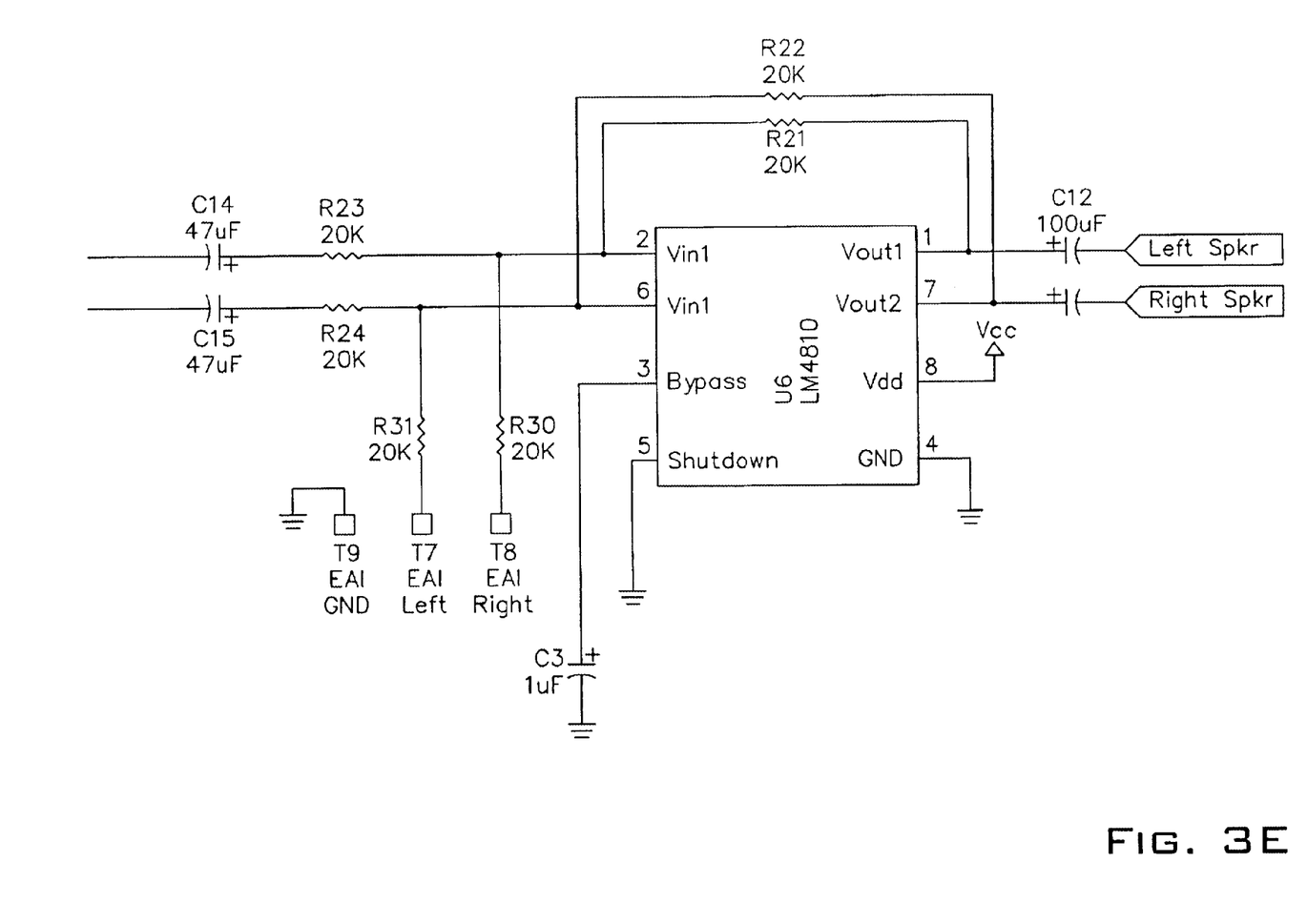

A block diagram of one preferred implementation of the circuit 24 is shown in FIG. 2, and a schematic diagram of the circuit 24 is shown in FIG. 3. It should be understood that the present invention should not be limited to the implementation shown in FIG. 3. Changes can be made to the component values, arrangements of components as well as source of components so long as the circuit 24 functions in the manner set forth herein.

The circuit 24 is provided with a pre-amplifier 44, a digital potentiometer 46, a microcontroller 48, a speaker driver amplifier 50, a power control 52, a power supply 54 and a peak detector 56.

As will be understood by those skilled in the art, the electrical sound signals produced by the microphones 22a and 22b are low voltage signals. The pre-amplifier 44 amplifies the voltage of the electrical sound signals produced by the microphones 22a and 22b. The gain of the pre-amplifier 44 can vary depending on a desired voltage level. It has been found that a suitable gain for the pre-amplifier 44 is about 40 V/V. The pre-amplifier 44 is also provided with a low-pass filter tuned to attenuate high frequency signals that 1) an individual's ear cannot detect, or 2) unnecessarily rob the circuit 24 of power. The low-pass filter of the pre-amplifier 44 can be tuned to any suitable frequency that provides a pleasing tone to the individual. It has been found that a suitable cutoff frequency for the low-pass filter is about 8 kHz. The pre-amplifier 44 can be implemented as an operational amplifier circuit having a feedback capacitor tuned to attenuate the high frequency signals. Although the pre-amplifier 44 is shown in FIG. 2 for purposes of clarity as one pre-amplifier, it should be understood that the pre-amplifier 44 is preferably implemented as two separate amplifiers with one amplifier for the microphone 22a (left microphone) and one amplifier for the microphone 22b (right microphone). The pre-amplifier 44 outputs amplified signals over signal paths 60a and 60b.

The amplified signals output by the pre-amplifier 44 are received by a first input of the digital potentiometer 46. A second input of the digital potentiometer 46 is connected to a virtual ground 62, and a "wiper" of the digital potentiometer 46 is connected to the microcontroller 48 via a signal path 64. The "wiper" selects a percentage of the amplified signal output by the pre-amplifier 44 to be passed to the speaker driver amplifier 50 via signal paths 68a and 68b. The percentage can range from 0% to 100%.

In one preferred embodiment, the digital potentiometer 46 has 256 steps and the signal received from the microcontroller 48 via the signal path 64 is a serial data stream. For example, if the "wiper" of the digital potentiometer 46 is set at 128, then 50% of the amplified signal is output by the digital potentiometer 46 and passed to the speaker driver amplifier 50 via the signal paths 68a and 68b. Although the digital potentiometer 46 is shown in FIG. 2 for purposes of clarity as one digital potentiometer, it should be understood that the digital potentiometer 46 is preferably implemented as a dual digital potentiometer with one digital potentiometer for the microphone 22a (left microphone) and one digital potentiometer for the microphone 22b (right microphone). Each of the digital potentiometers 46 are controlled independently by the microcontroller 48 so that the percentages of the amplified signals passed through the digital potentiometers 46 can be either the same or different. The digital potentiometer 46 for the right microphone 22b forms a right channel, and the digital potentiometer 46 for the left microphone 22a forms a left channel.

The signals output by the digital potentiometer 46 via the signal paths 68a and 68b are received by the speaker driver amplifier 50. The speaker driver amplifier 50 drives the speakers 20a and 20b. The speaker driver amplifier 50 is typically implemented as an integrated circuit.

The circuit 24 is provided with an external audio input having a left channel 70a and a right channel 70b so that an individual can connect an external audio device, such as a portable tape player or a Compact Disc player to the apparatus 10 and listen to audio while simultaneously receiving input from the left and right microphones 22a and 22b via the pre-amplifier 44 and the digital potentiometer 46. The left channel 70a and the right channel 70b are connected to the speaker driver amplifier 50 via resistors and capacitors to provide a fixed amount of attenuation of the signals provided on the left and right channels 70a and 70b. The volume of the audio provided through the left and right channels 70a and 70b can be controlled by varying the volume of the external audio device rather than by modifying the volume of the apparatus 10 with the control device 26. The amount of attenuation of the external audio signal can be varied depending on the magnitude of the external audio signal, the gain of the speaker driver amplifier 50, the characteristics of the speakers 20a and 20b as well as the desired maximum volume level. When the gain of the speaker driver amplifier 50 is about unity and a maximum volume level is about 82 db, it has been found that a suitable amount of attenuation of the audio signal provided by the external audio device is between about 99% and 90% (i.e., 1% to 10% of the audio signal is passed to the speaker driver amplifier 50).

As will be discussed in more detail below, the microcontroller 48 samples the amplified signals output by the pre-amplifier 44 to determine whether the amplified signals exceed a predetermined threshold value. If the amplified signals exceed the predetermined threshold value, the microcontroller 48 immediately outputs signals to the digital potentiometer 46 to reduce the volume levels of the signals being passed through the digital potentiometer 46. In this manner, sounds exceeding a predetermined threshold will be attenuated while sounds not reaching the predetermined threshold will not be attenuated. This permits the circuit 24 to reduce the overall amplification during loud sounds while permitting an amplification level selected by the volume control during lower level sounds.

The microcontroller 48 is provided with an A/D converter 74 for sampling the amplified signals output by the pre-amplifier 44. The A/D converter 74 samples at a pre-selected rate of about 62 kHz. To optionally ensure that a strong pulse in the amplified signal does not decay in between samples, the circuit 24 is provided with the peak detector 56. That is, the amplified signals output by the pre-amplifier 44 are fed to the peak detector 56 where the left and right channels are mixed and the mixed signal is peak held for a predetermined time period. The sample period (1/frequency) of the A/D converter 74 is the maximum time that could occur between a peak and a sample. The droop during the sample period must be less than the acceptable error allowed. The peak holding function of the peak detector 56 may be eliminated due to the rapid sampling period of the A/D converter 74. However, if a slower sampling period for the A/D converter 74 is implemented the peak holding function of the peak detector 56 can also be used.

As will be discussed in more detail below, the balance, volume and attenuation levels of the apparatus 10 are set by storing values in the microcontroller 48 (or associated computer readable medium, such as a memory external to the microcontroller 48, or the like) and selectively writing such values to the digital potentiometer 46. A right volume level variable is maintained for the volume level of the right channel and a left volume level variable is maintained for the volume level of the left channel of the digital potentiometer 46 so that the volume levels of the right and left channels are independently controlled. The microcontroller 48 is programmed to provide a plurality of separate volume levels for the apparatus 10. For example, the microcontroller 48 can be programmed to provide 10 volume levels, 20 volume levels or the like. A lookup table is stored in the microcontroller 48 (or associated computer readable medium) where 1) a volume level value and 2) an attenuation value is stored for each separate volume level. During normal conditions where the circuit 24 is not attenuating the electrical sound signals, the microcontroller 48 writes a volume level value to the digital potentiometers 46 for the right channel and the left channel.

For example, if the right volume level variable is set to 3, and the left volume level variable is set to 5, the volume level value for a volume setting of 3 is output to the digital potentiometer 46 for the right channel, and the volume level value for a volume setting of 5 is output to the digital potentiometer 46 for the left channel. To attenuate the electrical sound signals, the attenuation value for a volume setting of 3 is output to the digital potentiometer 46 for the right channel, and the attenuation value for a volume setting of 5 is output to the digital potentiometer 46 for the left channel.

For a volume level 1 (minimum volume), a volume level value of 0 may be stored, and for a volume level 20 (maximum volume) a volume level value of 255 may be stored for a 256 step digital potentiometer 46. Volume level values for the remaining volume levels 2–19 are provided between the minimum volume level value and the maximum volume level value. The volume level values stored in the microcontroller 48 can be selected to provide any desired transfer function. The volume level values are preferably selected to approximate a 2 db–3 db logarithmic decay of the volume levels. However, the volume level values can be spaced linearly or randomly between the minimum and volume level and the maximum volume level to provide any desired transfer function.

It should be noted that the input impedance of the speaker driver amplifier 50 is only about twice the output impedance of the digital potentiometer 46 thereby introducing a gain error. Thus, if the digital potentiometer 46 is set at 50% the output of the speaker driver amplifier 50 will not be set at 50%. The gain error can be eliminated by providing a buffer stage between the digital potentiometer 46 and the speaker driver amplifier 50. However, adding a buffer stage increases the cost of the circuit 24. Thus, the gain error is taken into account when determining the volume level values.

The attenuation values are also selected to provide a desired amount of attenuation or enhancement for the apparatus 10. It should be understood that the attenuation values can vary depending on the desired amount of attenuation of signals exceeding the predetermined threshold. Moreover, it should be understood that the attenuation values can exceed the volume level values. For example, the attenuation values can exceed the volume level values if it is desired to not let any sound come in unless the sound exceeded a certain level. This might be useful is an individual had to work next to a noisy machine and the individual wanted to block out this noise for comfort but if a loud sound such as a warning indicator was present, the signal would be allowed to pass through. In this case, the attenuation values would be selected so that no signal would go above about 82 db and the volume level values would be set to zero.

When the on/off button 30 is pressed on the control device 26, a signal is transmitted to the power control 52 via a signal path 76. The power control 52 momentarily gates power to the microcontroller 48 via a signal path 78. In response thereto, the microcontroller 48 toggles the power control 52 via a signal path 80 to maintain the power on. This provides the microcontroller 48 with the ability to automatically turn-off the apparatus 10 by again toggling the power control 52 via the signal path 80.

Figure 4:
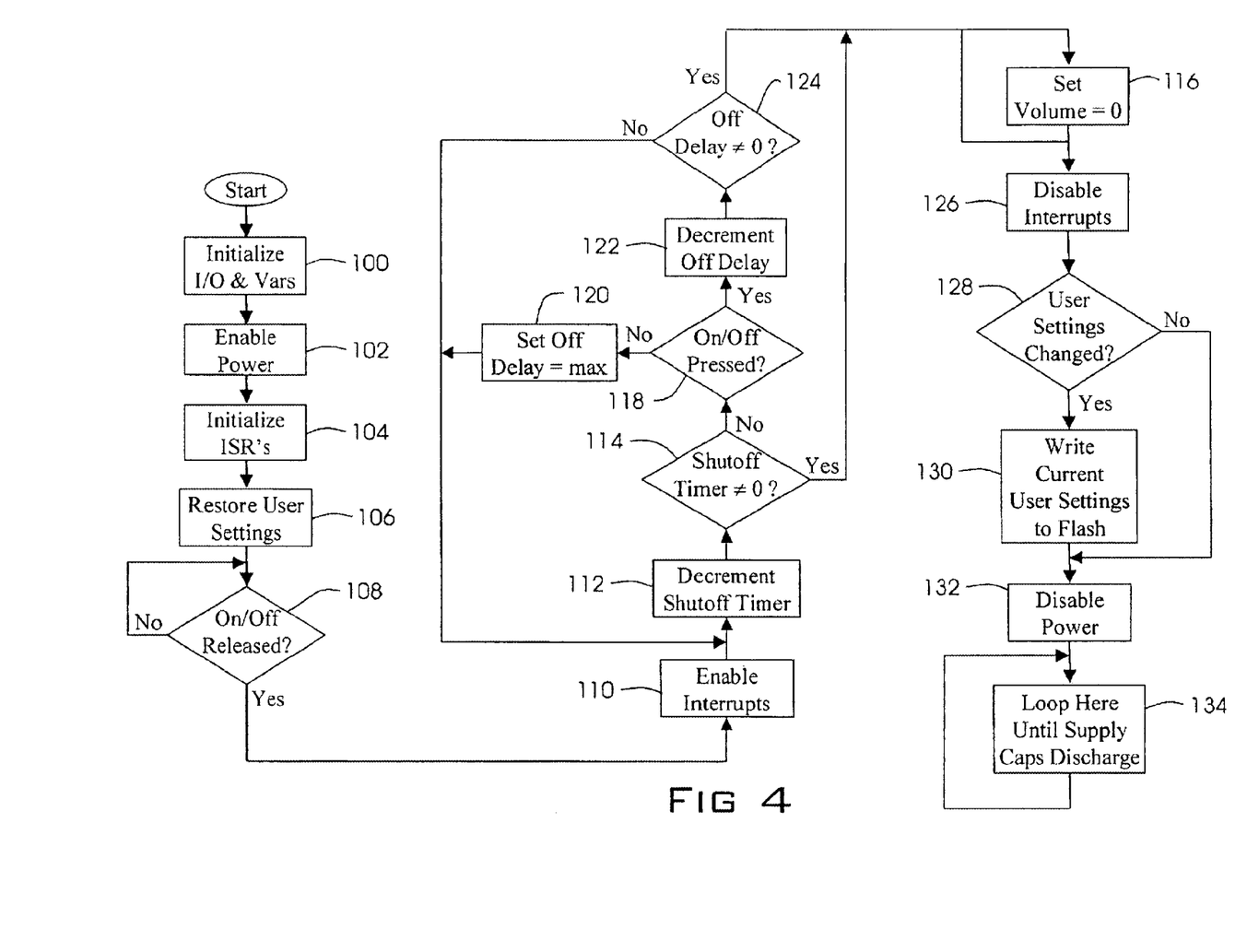
FIG. 4 is a flow diagram of a main loop of a method developed in accordance with the present invention.

Referring now to FIG. 4, shown therein is a flow chart of a main loop of a software program executing on the microcontroller 48. Upon receiving power from the power control 52, the microcontroller 48 branches to a step 100 where the microcontroller 48 initializes the input output ports and miscellaneous variables and timers to specify the topology for the circuit 24. The microcontroller 48 then branches to a step 102 where the microcontroller 48 enables power by writing a signal out to a port thereby toggling the power control 52, as discussed above. The microcontroller 48 branches to a step 104 to initialize the interrupt service routines, and then branches to a step 106 to restore user settings, such as the volume and/or balance settings. The user settings are typically stored in on-board rewritable memory, although the user settings can be stored on a separate memory chip.

Figure 5:
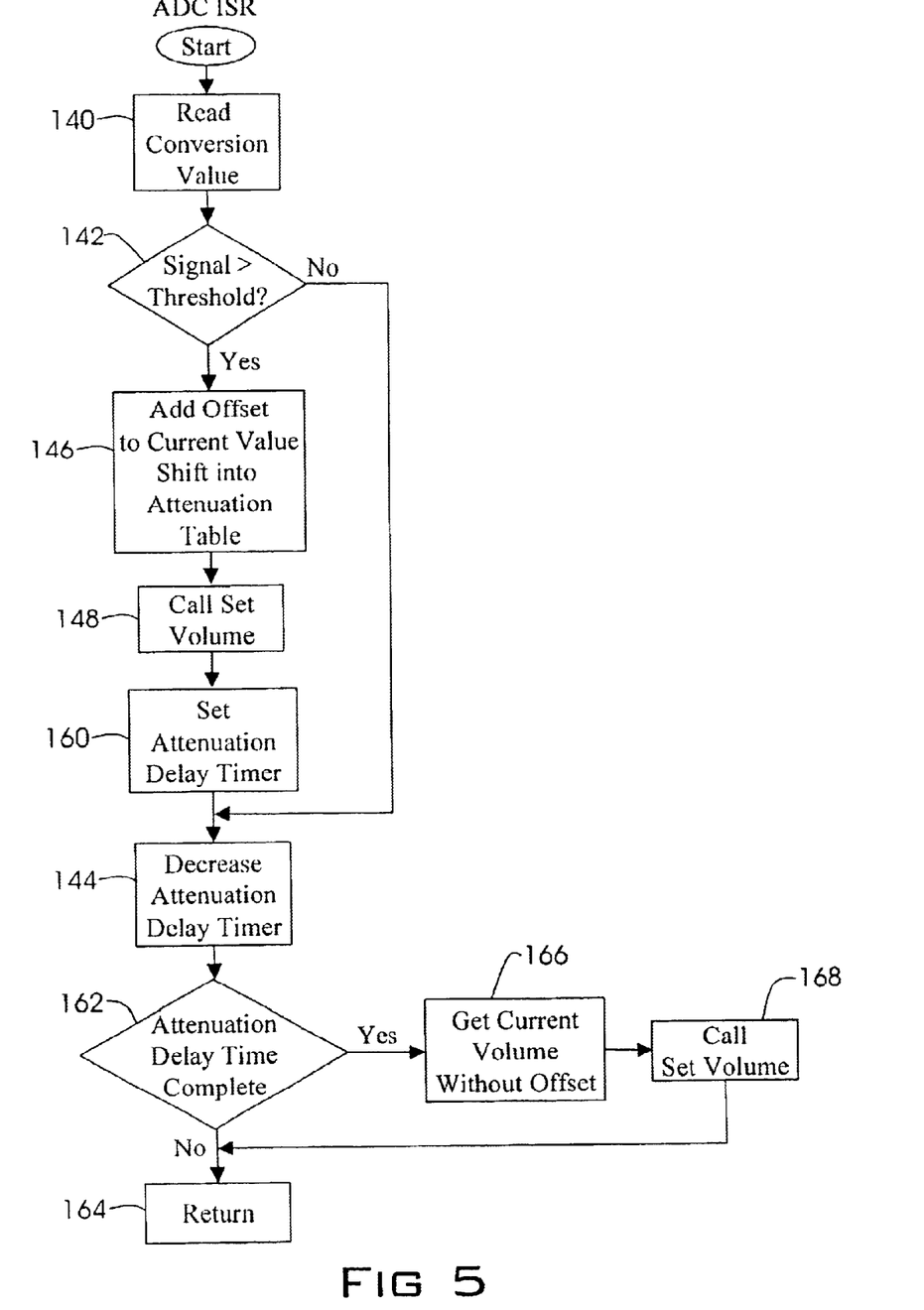
FIG. 5 is a flow diagram of an Analog to Digital Interrupt Service Routine constructed in accordance with the present invention.
Figure 6:
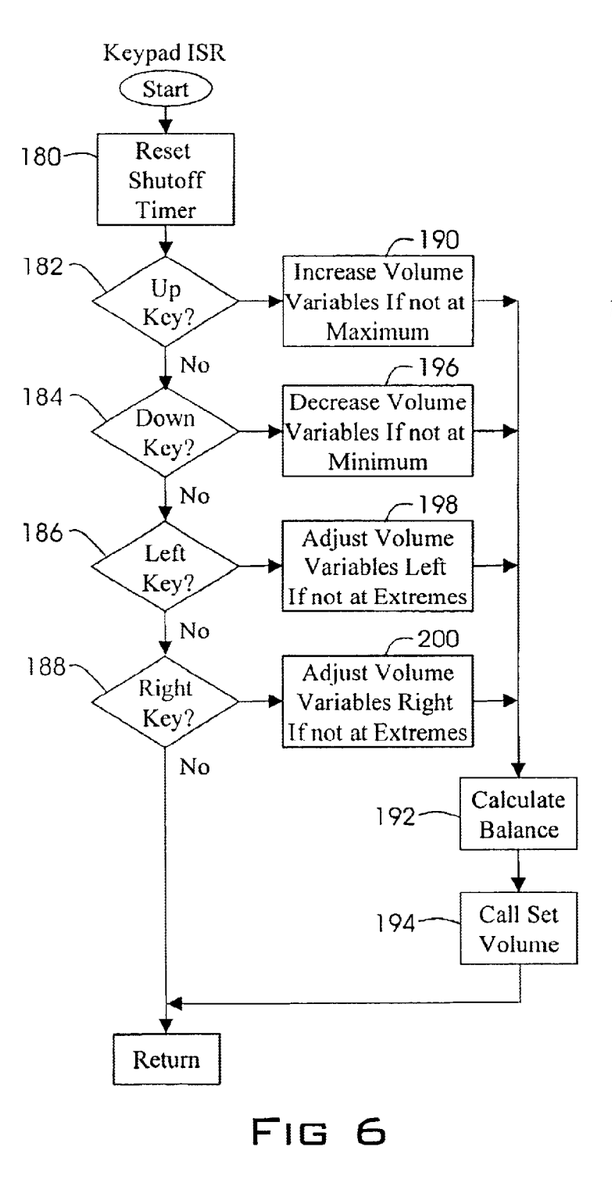
FIG. 6 is a flow diagram of a Keypad Digital Interrupt Service Routine constructed in accordance with the present invention.

The microcontroller 48 then checks to see if the on/off button 30 has been released at a step 108. If not, the microcontroller 48 loops back to the step 108 to check again. If the on/off button 30 has been released, the microcontroller 48 branches to a step 110 to enable interrupts. The software program enables two interrupts: a keypad ISR (a block diagram of which is shown in FIG. 6, and an Analog-to Digital converter ISR (ADC ISR) (a block diagram of which is shown in FIG. 5).

The microcontroller 48 then branches to a step 112 to decrement a shut off timer for automatically shutting off the apparatus 10 after a predetermined time period of for example, 20 minutes, 1 hour, 2 hours, 3 hours or 4 hours. Thus, if the individual forgets to shut off the apparatus 10, the microcontroller 48 will automatically shut off the apparatus 10 after the predetermined time period has elapsed to help conserve the power supply 54. The microcontroller 48 then branches to a step 114 where the microcontroller 48 determines whether the shutoff timer=0. If so, the microcontroller 48 branches to a step 116 to begin shutting off the apparatus 10.

If not, the microcontroller 48 branches to a step 118 to determine whether the on/off button 30 has been pressed. If the on/off button 30 has not been pressed, the microcontroller 48 branches to a step 120 where the microcontroller 48 sets an off delay timer to a maximum value and then branches to the step 112. The off delay timer prevents the inadvertent shutting off of the apparatus 10 by making the individual hold the on/off button for a predetermined time period, for example. If the on/off button 30 has been pressed, the microcontroller 48 branches to a step 122 where the off delay timer is decremented. The microcontroller 48 then branches to a step 124 where the microcontroller 48 checks whether the off delay timer=0. If not, the microcontroller 48 branches to the step 112, and if so, the microcontroller 48 branches to the step 116 to shut off the apparatus 10.

At the step 116, the volume of the apparatus 10 is set to 0 in both the right channel and the left channel by writing a data stream representing a 0 value to the digital potentiometer 46. The microcontroller 48 then branches to a step 126 where the interrupts are disabled followed by a step 128 where the microcontroller 48 determines whether user settings have changed. If the user settings have changed, the microcontroller 48 branches to a step 130 where current settings are written into the rewritable or flash memory. If not, the microcontroller 48 branches to a step 132 where power is disabled by toggling the signal path 80. The microcontroller 48 then branches to a step 134 where the microcontroller 48 loops until all of the power is discharged from the power control 52.

Shown in FIG. 5 is a flow chart of the ADC ISR subroutine. The microcontroller 48 first reads a conversion value from the A/D converter 74 at a step 140. The microcontroller 48 then branches to a step 142 where the microcontroller 48 determines whether the conversion value is greater than a predetermined threshold value. If not, the microcontroller 48 branches to a step 144 and the attenuation of the digital potentiometer 46 is not changed. If the conversion value is greater than the predetermined threshold value, the microcontroller 48 branches to a step 146 where an offset number is added to the volume level of the right channel to provide a modified right channel index variable, and the offset number is also added to the volume level of the left channel to provide a modified left channel index variable.

The microcontroller 48 then branches to a step 148 where the modified right channel index variable is passed to a right set volume routine, and the modified left channel index variable is passed to a left set volume routine. The left and right set volume routines are similar in construction and function. Thus, only one of the left and right set volume routines will be discussed herein for purposes of clarity.

Figure 7:
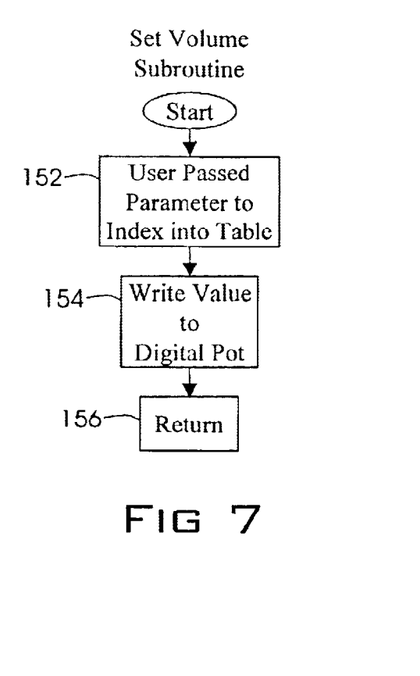
FIG. 7 is a flow diagram of a set volume subroutine constructed in accordance with the present invention.

The left set volume routine is shown in FIG. 7. Once the microcontroller 48 branches into the set volume routine, the microcontroller 48 branches to a step 152 where the modified left channel index variable is used as an index to retrieve an attenuation value for the left channel. The microcontroller 48 then branches to a step 154 where the attenuation value for the left channel is written to the digital potentiometer 46. The microcontroller 48 then branches to a step 156 where the microcontroller 48 exits the set volume routine. The left and right set volume routines could be combined into a single routine.

The microcontroller 48 then branches to a step 160 where the microcontroller 48 sets an attenuation delay timer which sets a time period in which the output of the digital potentiometer 46 will be attenuated. The time period of the attenuation delay timer can vary widely, but it has been found by Applicant's that a suitable time period is in the range from about 300 ms to about 500 ms. Desirably, the time period of the attenuation delay timer is set for about a 400 ms delay.

The microcontroller 48 then branches to the step 144 where the attenuation delay timer is decremented. The microcontroller 48 then branches to a step 162 where the microcontroller 48 determines whether the attenuation delay timer is completed. If not, the microcontroller 48 branches to a step 164 and thereby returns from the ADC ISR. If the attenuation delay timer is completed, then the microcontroller 48 branches to a step 166 to reset the normal volume levels. More specifically, at the step 166, the microcontroller 48 retrieves the volume level for the right channel and the volume level for the left channel.

The microcontroller 48 then branches to a step 168 where the volume level for the right channel is passed to the right channel set volume routine and the volume level for the left channel is passed to the left channel set volume routine. Only one of the left and right set volume routines will be discussed herein for purposes of clarity. Once the microcontroller 48 branches into the set volume routine, the microcontroller 48 branches to the step 152 where the volume level for the right channel is used to retrieve a volume level value for the right channel. The microcontroller 48 then branches to the step 154 where the volume level values for the right channel is written to the digital potentiometer 46. The microcontroller 48 then branches to the step 156 where the microcontroller 48 exits the set volume routine. The microcontroller 48 then branches to the step 164 to return from the ADC ISR.

The microcontroller 48 also executes a keypad ISR, which is shown in FIG. 6, for setting the volume and the balance of the apparatus 10. When one of the up-volume button 32, down-volume button 32, left balance button 36, and right balance button 38 is pressed a signal internal to the microcontroller 48 for the duration of the up-volume button 32, down-volume button 32, left balance button 36, or right balance button 38 being pressed is generated. The keypad ISR is executed on a level of the signal, rather than on an edge of the signal thereby re-interrupting the microcontroller 48 when the up-volume button 32, down-volume button 32, left balance button 36, or right balance button 38 are held down. Once the keypad ISR is executed, the microcontroller 48 branches to a step 180 where the shutoff timer is reset to a predetermined value.

The microcontroller 48 then sequentially branches to the steps 182, 184, 186 and 188 where the microcontroller 48 determines whether the up-volume button 32, down-volume button 32, left balance button 36, or right balance button 38 are being pressed.

To set the volume of the left and right channels, as well as the balance the microcontroller 48 is programmed with a desired right volume level variable, and a desired left volume level variable. The desired right volume level variable and the desired left volume level variable are permitted to become negative so that the microcontroller 48 can keep track of the balance.

If the up-volume button 32 is being pressed, the microcontroller 48 branches to a step 190 where the microcontroller 48 checks the values of the desired right volume level variable and the desired left volume variable. If neither of the desired right volume level variable for the right channel and the desired left volume level variable for the left channel are above the maximum volume level, such as 20, the microcontroller 48 increments the desired right volume level variable for the right channel and the desired left volume level variable for the left channel. The microcontroller 48 then branches to a step 192 where the microcontroller 48 calculates a balance for the apparatus 10, and then branches to a step 194 where the microcontroller 48 calls the set volume routine for setting the volume level for the right channel and the left channel as discussed above. The step 192 will be discussed in more detail below.

If the down-volume button 34 is being pressed, the microcontroller 48 branches to a step 196 where the microcontroller 48 checks the values of the desired right volume level variable and the desired left volume variable. If either of the desired right volume level variable for the right channel and the desired left volume level variable for the left channel are above the minimum volume level, such as 0, the microcontroller 48 decrements the desired right volume level variable for the right channel and the desired left volume level variable for the left channel.

If the left balance button 36 is being pressed, the microcontroller 48 branches to a step 198 where the microcontroller 48 checks the values of the desired right volume level variable and the desired left volume variable. The desired right volume level variable for the right channel is decremented if the desired right volume variable is not already at the minimum volume level, such as 0. The desired left volume level is incremented if the desired left volume level is not already at the maximum volume level, such as 20.

If the right balance button 38 is being pressed, the microcontroller 48 branches to a step 200 where the microcontroller 48 checks the values of the desired right volume level variable and the desired left volume variable. The desired right volume level variable for the right channel is incremented if the desired right volume level variable is not already at the maximum level. The desired left volume level variable for the left channel is decremented if the desired left volume level variable is not already at the minimum level.

At the step 192, the microcontroller 48 checks the value of the desired right volume level variable. If the desired right volume level variable is equal to or greater than zero, the right volume level variable is set to be equal to the desired right volume level variable. If the desired right volume level variable is less than zero, the right volume level variable is set to zero. The microcontroller 48 also checks the value of the desired left volume level variable. If the desired left volume level variable is equal to or greater than zero, the left volume level variable is set to be equal to the desired left volume level variable. If the desired left volume level variable is less than zero, the left volume level variable is set to zero.

The volume level of the apparatus 10 is then set at the step 194 by passing the left and right volume level variables to the set volume subroutine, as discussed above.

As will be recognized by those skilled in the art, the apparatus 10 has many advantages over the prior art. For example, the apparatus 10 utilizes low cost and low power components thereby decreasing the cost of the apparatus 10 while increasing the time periods in between battery changes. Moreover, the lookup tables stored in the microcontroller 48 can be selectively customized for customers without modification of the hardware.

Changes may be made in the embodiments of the invention described herein, or in the parts or the elements of the embodiments described herein, or in the steps or sequence of steps of the methods described herein, without departing from the spirit and/or the scope of the invention as defined in the following claims.

What is claimed is:

1. An earmuff, comprising:
   a headpiece for supporting the earmuff on the head of an individual; and
   a circuit having an input device for receiving external sound energy and converting the external sound energy to electrical sound signals, wherein the circuit further comprises:
   a pre-amplifier for amplifying and attenuating the electrical sound signals;
   a peak detector for detecting and holding a maximum value of the amplified electrical sound signals;
   a microcontroller for sampling the electrical sound signals from the pre-amplifier so as to determine whether the electrical sound signals from the pre-amplifier exceed a predetermined threshold value;
   a power control for controlling, maintaining, and transmitting power to the microcontroller;
   a digital potentiometer for receiving the electrical sound signals from the pre-amplifier and reducing the volume levels of the electrical sound signals;
   a speaker driver amplifier for providing a fixed amount of attenuation to external audio signals; and
   a power supply for providing power to the circuit.

* * * * *